(12) United States Patent
Gazeley et al.

(10) Patent No.: US 10,653,840 B2
(45) Date of Patent: May 19, 2020

(54) HOUSING AND DRUG DELIVERY DEVICE HEREWITH

(71) Applicant: Sanofi, Paris (FR)

(72) Inventors: Oliver Charles Gazeley, Leamington Spa (GB); Paul Richard Draper, Evesham (GB)

(73) Assignee: Sanofi, Paris (FR)

( * ) Notice: Subject to any disclaimer, the term of this patent is extended or adjusted under 35 U.S.C. 154(b) by 426 days.

(21) Appl. No.: 15/514,997

(22) PCT Filed: Oct. 9, 2015

(86) PCT No.: PCT/EP2015/073444
§ 371 (c)(1),
(2) Date: Mar. 28, 2017

(87) PCT Pub. No.: WO2016/055636
PCT Pub. Date: Apr. 14, 2016

(65) Prior Publication Data
US 2018/0228976 A1   Aug. 16, 2018

(30) Foreign Application Priority Data
Oct. 9, 2014  (EP) .................................... 14306600

(51) Int. Cl.
*A61M 5/24* (2006.01)
*A61M 5/315* (2006.01)
(Continued)

(52) U.S. Cl.
CPC .......... *A61M 5/24* (2013.01); *A61M 5/31541* (2013.01); *A61M 5/31543* (2013.01);
(Continued)

(58) Field of Classification Search
CPC ..................... A61M 5/326; A61M 2005/2411; A61M 5/24; A61M 5/31541; A61M 5/31543
See application file for complete search history.

(56) References Cited

U.S. PATENT DOCUMENTS

2009/0275914 A1* 11/2009 Harms ..................... A61M 5/24
604/506
2014/0046266 A1* 2/2014 Schneider ............... A61M 5/24
604/187

FOREIGN PATENT DOCUMENTS

DE    10 2009 048479    3/2011
EP         2274030       1/2011
(Continued)

OTHER PUBLICATIONS

International Search Report and Written Opinion in International Application No. PCT/EP2015/073444, dated Apr. 11, 2017, 8 pages.
(Continued)

*Primary Examiner* — Rebecca E Eisenberg
*Assistant Examiner* — Melissa A Snyder
(74) *Attorney, Agent, or Firm* — Fish & Richardson P.C.

(57) ABSTRACT

The present disclosure is generally directed to a drug delivery device for selecting and dispensing a number of user variable doses of a medicament and a housing for such a device. The housing for the drug delivery device comprises an outer housing, a housing insert, which is rotationally constrained to the outer housing and guided axially movable relative to the outer housing, and a cartridge holder. The cartridge holder is attachable to the distal end of the outer housing by at least one groove and at least one lug. The cartridge holder comprises proximally facing ramps and the housing insert comprises corresponding, distally facing ramps. The groove comprises a first sloped portion inclined such that upon a rotational attaching movement, the cartridge holder is moved proximally relative to the outer (Continued)

housing and a second sloped portion inclined such that upon a rotational attaching movement, the cartridge holder is moved distally relative to the outer housing. The proximally facing ramps and the distally facing ramps engage at least when the lug is in the second sloped portion of the groove and are inclined such that the housing insert is moved proximally relative to the outer housing and the cartridge holder upon an attaching movement of the cartridge holder.

20 Claims, 3 Drawing Sheets

(51) Int. Cl.
  *A61M 5/20*   (2006.01)
  *A61M 5/31*   (2006.01)
(52) U.S. Cl.
  CPC ..... *A61M 5/31551* (2013.01); *A61M 5/31571* (2013.01); *A61M 5/31583* (2013.01); *A61M 2005/2026* (2013.01); *A61M 2005/2407* (2013.01); *A61M 2005/2488* (2013.01); *A61M 2005/3126* (2013.01); *A61M 2205/581* (2013.01); *A61M 2205/582* (2013.01)

(56) References Cited

FOREIGN PATENT DOCUMENTS

| | | |
|---|---|---|
| WO | WO 2009/132781 | 11/2009 |
| WO | WO 2012/130704 | 10/2012 |
| WO | WO 2014/033195 | 3/2014 |

OTHER PUBLICATIONS

International Preliminary Report on Patentability in International Application No. PCT/EP2015/073444, dated Apr. 11, 2017, 7 pages.

\* cited by examiner

HOUSING AND DRUG DELIVERY DEVICE HEREWITH

CROSS-REFERENCE TO RELATED APPLICATIONS

This application is a U.S. national stage application under 35 USC § 371 of International Application No. PCT/EP2015/073444, filed on Oct. 9, 2015, which claims priority to European Patent Application No. 14306600.9 filed on Oct. 9, 2014, the entire contents of which are incorporated herein by reference.

TECHNICAL FIELD

The present disclosure is generally directed to a drug delivery device for selecting and dispensing a number of user variable doses of a medicament and a housing for the drug delivery device.

Pen type drug delivery devices are applicable where regular injections by persons without formal medical training occur. This may be increasingly common among patients with diabetes where self-treatment enables such patients to effectively manage their disease. In practice, such a drug delivery device allows a user to individually select and dispense a number of user variable doses of a medicament. Certain aspects are not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some embodiments are directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

In some embodiments, an advantage may be to provide an improved resettable drug delivery device and a respective housing.

In some aspects, a housing for a drug delivery device comprises an outer housing with a distal end and an opposite proximal end, a housing insert, which is rotationally constrained to the outer housing and guided axially movable relative to the outer housing, and a cartridge holder, which is attachable to the distal end of the outer housing by corresponding coupling parts, for example bayonet coupling parts, on the cartridge holder and on the outer housing. The coupling parts may comprise at least one groove provided on one of the cartridge holder and on the outer housing and at least one lug provided on the other of the cartridge holder and on the outer housing. Preferably, the cartridge holder comprises proximally facing ramps and the housing insert comprises corresponding distally facing ramps. In a first embodiment the at least one groove comprises a first sloped portion inclined such that the cartridge holder is moved proximally relative to the outer housing upon an attaching movement and a second sloped portion inclined such that the cartridge holder is moved distally relative to the outer housing upon an attaching movement.

The preferred helical path of the first (bayonet) grooves moves the cartridge holder axially, in a proximal direction relative to the outer housing, which causes compression between the cartridge bung and the bearing of the piston rod. The second sloped groove is sloped such that the preferred helical path moves the cartridge holder axially, in a distal direction relative to the outer housing, which reduces the compression between the cartridge bung and the bearing of the piston rod. It is preferable, to achieve zero compression and zero clearance of the cartridge bung and the bearing of the piston, such that the amount of distal displacement is exactly equal to the amount of compression of the bung. Therefore, the axial length of the second sloped portion needs to be equal to the axial length of the first sloped portion between the point at which the drive sleeve is engaged by the reset plate and the first flat portion. Taking into account that due to e.g. material and manufacturing tolerances a zero compression and a zero clearance of the cartridge bung and the bearing is only theoretically achievable, certain aspects are intended to minimize compression and clearance by adapting the length of the first and second sloped portions accordingly.

Further, the proximally facing ramps and the distally facing ramps may engage at least when the at least one lug is in the second sloped portion of the at least one groove and may be inclined such that the housing insert is moved proximally relative to the outer housing and/or the cartridge holder upon an attaching movement of the cartridge holder. In other words, the interface between the outer housing and the cartridge holder is designed such that attaching the cartridge holder to the outer housing results in a proximal movement of the cartridge holder relative to the outer housing followed by a distal relative movement. This opposite distal movement may be used to remove compression or stress within component parts of a drug delivery device. In addition, this serves as a safety mechanism preventing that the cartridge holder is unintendedly detached from the outer housing by applying an axial load on the cartridge holder. The design of the ramps is chosen such that the housing insert moves with a different speed and/or in a different direction compared with the cartridge holder during a stage of the attachment when the cartridge holder moves in the distal direction relative to the outer housing. Thus, the movement of the housing insert may be used to couple or de-couple component parts of a drug delivery device during this stage of the attachment.

A sloped portion of a groove is preferably a portion extending in a plane neither perpendicular nor parallel to the longitudinal axis of the outer housing. For example, a sloped portion may extend along a helical path on a surface of the cartridge holder or the outer housing. In contrast to a sloped portion, a flat portion is preferably a portion extending in a plane perpendicular to longitudinal axis of the outer housing, while a vertical portion is preferably a portion extending in a plane parallel to longitudinal axis. In other words, if the lug engages a sloped portion of the groove the cartridge holder performs a combined rotational and axial movement relative to the outer housing, if the lug engages a flat portion of the groove the cartridge holder performs only a rotational movement relative to the outer housing, and if the lug engages a vertical portion of the groove the cartridge holder performs only an axial movement relative to the outer housing.

The attaching movement may include a relative rotation, a relative axial movement and/or a combination thereof. For example, an axial movement may be followed by a movement along a helical path which in turn may be followed by a rotational movement. The attaching movement is typically the movement the cartridge holder performs relative to the outer housing when fastening the cartridge holder to the outer housing.

The stationary outer housing is a fixed basis for relative movements of the cartridge holder and/or the housing insert. The outer housing may have a tubular form with a circular cross-section. It may be a single component part or may comprise, in addition to the cartridge holder and the housing insert, additional parts. The housing insert is preferably axially guided within the outer housing to allow limited axial movement relative to the outer housing. It is rotationally secured to the outer housing, e.g. by engaging splines.

In a preferred embodiment the at least one groove further comprises at least one flat portion inclined such that the cartridge holder is not moved axially relative to the outer housing upon a rotational attaching movement. Preferably, the at least one groove comprises a first flat portion interposed between the first sloped portion and the second sloped portion and a second flat portion located after the second sloped portion in a rotational attaching movement. If the ramps are in engagement when the lug is in one of the flat portions, the axial movement of the housing insert occurs with a different speed and/or direction compared to a state when the lug is in one of the sloped portions. This variation in speed and/or direction may be used for different coupling or de-coupling actions.

According to a further embodiment, the at least one groove further comprises at least one vertical portion inclined such that the cartridge holder is not moved rotationally relative to the outer housing upon an attaching movement. Such a vertical portion is preferably located such that during the attachment process the lug is first of all guided in the vertical portion and only thereafter in a sloped or flat portion of the groove. In other words, for attachment of the cartridge holder to the outer housing a user has to push the cartridge holder onto or into the outer housing followed by a relative rotation of these two components, which may cause a relative axial movement.

Preferably, the housing further comprises at least one detent located on the outer housing and/or the cartridge holder such that the cartridge holder is rotationally locked to the outer housing when the at least one lug is in the second flat portion of the at least one groove. This may additionally secure the cartridge holder on or in the outer housing and prevent unintended detachment.

In some cases, it may be desirable if the housing insert movement is caused by the cartridge holder entraining or pushing the housing insert. This may be achieved with the proximally facing ramps and the distally facing ramps not engaging when the at least one lug is in the first sloped portion of the at least one groove. In other words, the ramps may be distributed spaced in circumferential direction such that the ramp surfaces do not contact each other, whereas axially facing surfaces of the housing insert and the cartridge holder are in contact.

The position and movements of the housing insert may be controlled by providing at least one spring biasing the housing insert in the distal direction. This results in retaining the housing insert in a defined distal position as long as the cartridge holder is detached from the outer housing and further moving the housing insert during attachment of the cartridge holder. In addition, such a spring forces the housing insert to move opposite to the attachment movement upon detachment of the cartridge holder from the outer housing.

According to a further aspect, in a housing comprising an interface with a groove and a lug and an interface with ramps on the cartridge holder and the outer housing and/or housing insert, the above mentioned locking detent and the at least one spring biasing the housing insert in the distal direction and/or a further spring the pitches of the first and second sloped portions and the cam slopes of the ramps are selected preferably such that the cartridge holder under the action of at least one spring overhauls the cam interface of the ramps and the interface of groove and lug if the engagement is released by the user before reaching the locking detent. For example, if the ramps were not there or pitched incorrectly the clutch spring wouldn't be able to push the cartridge holder out of the device on the second sloped portion of the groove, or the first flat portion. The torque induced by the ramps is greater than the torque in the opposite direction induced by the sloped second portion of the groove. If the user let's go of the cartridge holder in the second sloped portion the action of the clutch spring needs to pull the cartridge holder first proximally, then purely rotationally, then distally.

A drug delivery device is suitable for selecting and dispensing a number of user variable doses of a medicament and comprises a housing as defined above. The device typically comprises the housing, a dose setting element, a drive member coupled to the dose setting member via a clutch and a piston rod coupled to the outer housing and to the drive member. Preferably, the dose setting member is rotatable relative to the outer housing during dose setting, i.e. increasing or decreasing the dose, and dose dispensing between a minimum dose position and a maximum dose position. The drive member may be rotationally coupled to the dose setting member via a slipping clutch during dose setting and rotationally constrained to the dose setting member during dose dispensing. The housing insert may be a reset element which is preferably axially constrained to the dose setting element. In addition, the device may comprise at least one spring acting on the reset element, such that, if the cartridge holder is detached from the outer housing, the reset element is axially moved relative to the outer housing into a position in which the dose setting element is rotationally constrained to the outer housing and the drive member is allowed to rotate relative to the outer housing. In other words, detachment of the cartridge holder from the outer housing allows an axial movement of the reset element and, preferably, the dose setting element into a resetting position, in which the drive member may be rotated relative to the outer housing and relative to the dose setting member. As the piston rod is coupled to the outer housing and to the drive member, e.g. via a threaded interface with the outer housing and a splined interface with the drive member, resetting of the piston rod requires free rotation of the drive member. Thus, resetting of the drug delivery device may be performed simply by pushing back the piston rod or lead screw after removal of the cartridge holder.

If the cartridge holder is attached to the outer housing, the cartridge holder preferably moves the reset element and the dose setting element against the bias of the at least one spring into a position in which the dose setting element is rotatable relative to the outer housing. Thus, attachment of the cartridge holder locks the device in a dose setting and dose dispensing mode allowing dose setting and dose dispensing which requires rotation of the dose setting element relative to the outer housing.

In a preferred embodiment, the reset element is permanently rotationally constrained to the outer housing. This allows to rotationally lock or unlock component parts to the housing by engaging or disengaging the reset element. The axial movement of the reset element between the resetting mode and the dose setting and dose dispensing mode may be used to couple or decouple component parts to or from the outer housing.

According to an embodiment the drive member is axially movable relative to the outer housing between a dose setting position in which the drive member is rotationally constrained to the outer housing via the reset element and a dose dispensing position in which the drive member is rotatable relative to the reset element and the outer housing. In other words, the axial position of the drive member determines whether the device is in a dose setting mode allowing a user to increase or decrease a dose by rotation of the dose setting member without dispensing medicament or in a dose dispensing mode allowing a user to dispense a set dose by rotation of the dose setting element and the drive member. Preferably, the at least one spring biases the drive member into its dose setting position.

In a further development of this embodiment, the clutch between the dose setting element and the drive member is a slipping clutch with first clutch teeth on the drive member and second clutch teeth on a clutch plate, which is rotationally constrained to the dose setting element during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the bias of the clutch spring by allowing the sleeve and/or the clutch element to translate axially against the force of the clutch spring.

This may result in an oscillating axial movement of the sleeve and/or the clutch element due to continued disengagement and following re-engagement into the next detented position. An audible click may be generated by this re-engagement, and tactile feedback may be given by the change in torque input required.

The at least one spring may bias the drive member into abutment with the clutch plate. If the cartridge holder is detached from the outer housing, the at least one spring may bias the dose setting element into an axial position relative to the clutch plate in which the clutch plate and the dose setting element are rotationally de-coupled. This allows rotation of the drive member relative to the dose setting element without overcoming the slipping clutch.

Preferably, the clutch between the drive member and the dose setting element is a slipping clutch which allows relative rotation between the drive member and the dose setting element in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

The outer housing may comprise an inwardly protruding wall or web with a central opening and at least one further opening with one of the cartridge holder and the reset element comprising at least one axially extending finger or the like protrusion extending through the further opening. This allows imparting a force or movement from the cartridge holder to the reset element or vice versa. Preferably, the inwardly protruding wall or web comprises an inner thread wherein the piston rod is rotationally constrained to the drive member and comprises an outer thread engaging the inner thread.

The drug delivery device may further comprise at least one cartridge holder spring axially interposed between the cartridge holder and the inwardly protruding wall or web. This additional spring may compensate length tolerances of the cartridge and further bring the cartridge in a defined distal position.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

In another preferred embodiment, the drug delivery device further comprises a gauge element radially interposed between the outer housing and the dose setting element. The gauge element is axially movable relative to the outer housing and in threaded engagement with the dose setting element. The outer housing may comprise at least one aperture and the gauge element may comprise at least one aperture. If the dose setting element is a number sleeve which comprises markings on its outer surface, at least one of the markings is visible through the aperture in the gauge element and the aperture in the outer housing during dose setting and dose dispensing. The term aperture may include a simple opening the outer housing or gauge element or a transparent window or lens. A window in the outer housing may be incorporated using a 'twin-shot' molding technology. For example, the outer housing is molded during a 'first shot' in a translucent material, and the outer cover of the outer housing is molded during a 'second shot' in an opaque material.

The gauge element may be axially guided within the outer housing such that rotation of the dose setting element causes an axial displacement of the gauge element. The position of the gauge element may thus be used to identify the actually set and/or dispensed dose. Different colors of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the outer housing. The gauge element may have the form of a shield or strip extending in the longitudinal direction of the device. As an alternative, the gauge element may be a sleeve. In an embodiment, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow view only on a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the outer housing and relative to the outer housing. In other words, the dose setting element does not perform a translational movement during dose setting. This prevents that the dose setting element is wound out of the outer housing or that the outer housing has to be prolonged for covering the dose setting element within the outer housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The device may further comprise a dispensing button or trigger. The button is preferably a user operable element located proximally of the drive sleeve and the clutch element. When used in a drug delivery device, the button may extend from the proximal end of the device and, preferably, does not change its axial position during dose setting. The button is preferably coupled to a user operable dose selector and may be releasably coupled to a number sleeve component and/or a stationary housing component. In an alternative embodiment, the button may be part of a dose setting arrangement or may be the dose setting member. The button may be a multi-functional element having in addition to the above features e.g. a clicker feature.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. For example, the last dose protection mechanism comprises a nut member interposed between the drive member and the dose setting element (number sleeve) or any other component which rotates during dose setting and dose dispensing. In a preferred embodiment, the dose setting element rotates during dose setting and during dose dispensing, whereas the drive member only rotates during dose dispensing together with the dose setting element. Thus, in this embodiment, the nut member will only move axially during dose setting and will remain stationary with respect to these components during dose dispensing. Preferably, the nut member is threaded to the drive member and splined to the dose setting member. As an alternative, the nut member may be threaded to the dose setting member and may be splined to the drive member. The nut member may be a full nut or a part thereof, e.g. a half nut.

The injection device may comprise at least one clicker mechanism for generating a tactile and/or audible feedback. A feedback may be generated during dose setting (increasing and/or decreasing a dose), dose dispensing and/or at the end of dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments of the invention will now be described with reference to the accompanying drawings, in which.

DETAILED DESCRIPTION

Figure 1:
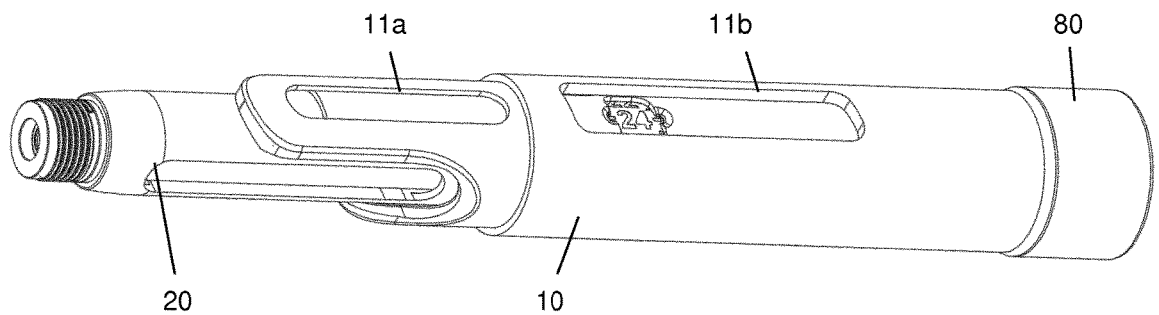
FIG. 1 shows a top view of a drug delivery device according to a first embodiment invention.
Figure 2:
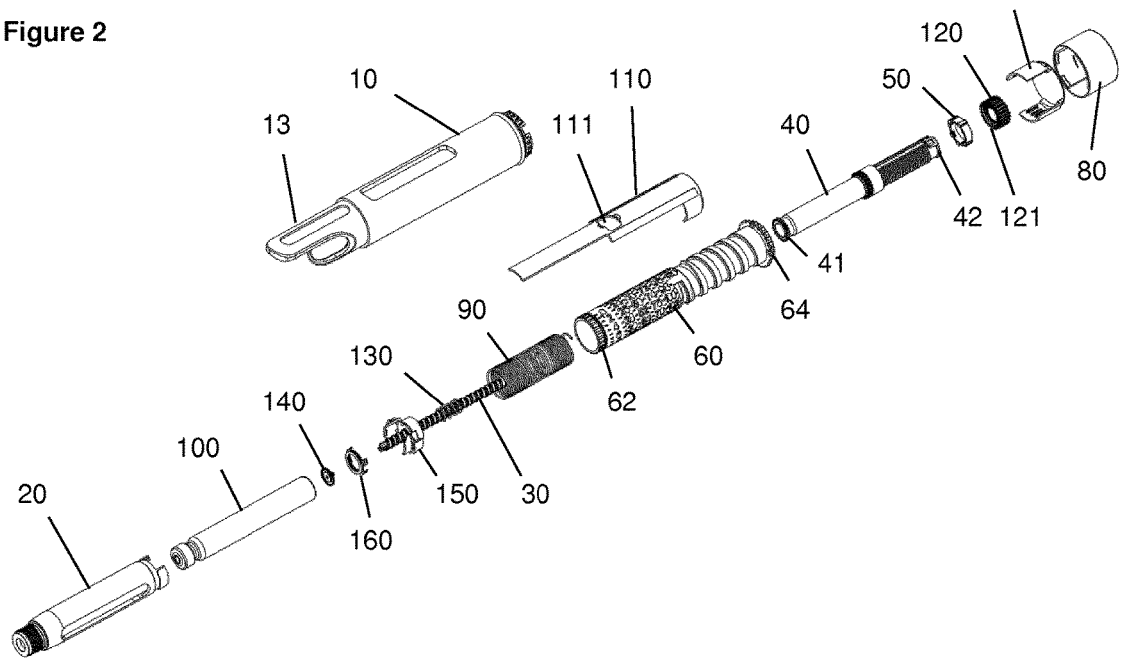
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or outer housing 10, a cartridge holder 20, a lead screw (piston rod) 30, a drive sleeve 40, a nut 50, a dose setting element which is a dose indicator (number sleeve) 60, a button 70, a dial grip or dose selector 80, a torsion spring 90, a cartridge 100, a gauge element 110, a clutch plate 120, a clutch spring 130, a bearing 140, a housing insert in the form of a reset plate 150 and a cartridge holder spring 160. A needle arrangement (not shown) with a needle hub and a needle cover may be provided as additional components, which can be exchanged as explained above. All components are located concentrically about a common principal axis I of the mechanism which is shown in FIG. 3.

The outer housing 10 or body is a generally tubular element having a proximal end with an enlarged diameter. The outer housing 10 provides location for the liquid medication cartridge 100 and cartridge holder 20, windows 11a, 11b for viewing the dose number on the dose indicator 60 and the gauge element 110, and a feature on its external surface, e.g. a circumferential groove, to axially retain the dose selector 80. A flange-like or cylindrical inner wall comprises an inner thread 12 engaging the piston rod 30. The outer housing 10 further has at least one internal, axially orientated slot or the like for axially guiding the gauge element 110. In the embodiment shown in the Figures, the distal end is provided with an axially extending strip 13 partly overlapping cartridge holder 20. The figures depict the housing 10 as a single outer housing component. However, the outer housing 10 could comprise two or more housing components which may be permanently attached to each other during assembly of the device.

Figure 3:
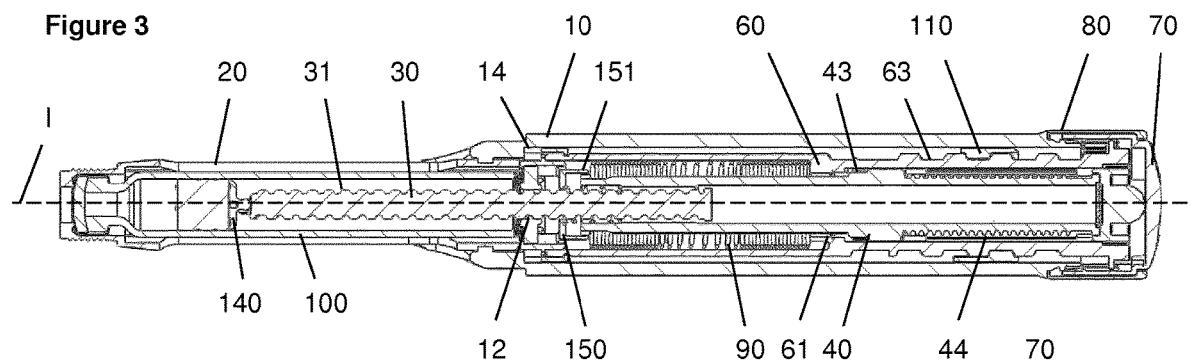
FIG. 3 shows a sectional view of the device of FIG. 1.

The cartridge holder 20 is located at the distal side of outer housing 10 and attached thereto in a releasable manner by a bayonet like coupling which is not shown in detail in the embodiment of FIGS. 1 to 3. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the outer housing 10. The cartridge holder 20 contains the replaceable cartridge 100 and acts to axially align the reset plate 150 spline teeth 151 with the drive sleeve 40 spline teeth 41. When the cartridge holder 20 is removed, the trigger spring 130 forces the reset plate 150 (and dose setting element 60) axially in a distal direction, disengaging the spline teeth 41, 151 between the reset plate 150 and the drive sleeve 40 and the spline teeth between the clutch plate 120 and the dose setting element 60, allowing the device to be reset.

The piston rod 30 is rotationally constrained to the drive sleeve 40 via a splined interface. When rotated, the piston rod 30 is forced to move axially relative to the housing 10, through its threaded interface with the housing 10. The piston rod 30 comprises an outer thread 31 engaging the inner thread 12 of the outer housing 10.

The drive sleeve 40 extends from the interface with the dose setting element 60 (via the clutch plate 120) down to a splined tooth interface 41, 151 (FIG. 6) with the reset plate 150. This provides a rotational constraint to the drive sleeve 40 during dose setting. When the button 70 is pressed, these spline teeth 41, 151 are disengaged allowing the drive sleeve 40 to rotate under the action of the drive spring 90, dispensing the set dose. Ratchet teeth 42 of the drive sleeve 40 and corresponding ratchet teeth 121 of the clutch plate 120 form a slipping clutch. Pressing the button 70 also engages an additional spline clutch 43, 61 between the drive sleeve 40 and dose setting element 60.

The last dose nut 50 is located between the dose setting element 60 and the drive sleeve 40. It is rotationally constrained to the dose setting element 60, via a splined interface. It moves along a helical path relative to the drive sleeve 40, via a threaded interface 44, when relative rotation occurs between the dose setting element 60 and drive sleeve 40 (during dialing and resetting only). FIG. 3 shows a state when the cartridge 100 is nearly empty and nut 50 is about to contact a stop on drive sleeve 40 to limit further dose setting.

The dose setting element 60 is constrained, via a clip at its distal end, to the reset plate 150 to allow rotation but not axial translation when in the dialing and dispense conditions. On entry to the reset condition the reset plate 150 and dose setting element 60 move axially in the distal direction, engaging a spline interface 62, 14 between the dose setting element 60 and the housing 10 to prevent rotation during reset. The dose setting element 60 is marked with a sequence of numbers, which are visible through opening 111 in the gauge element 110 and the slot-like window 11b in the housing 10, to denote the dialed dose of medicament.

The button 70 is splined to the dose setting element 60 when in the dose dialing condition. This spline interface is disconnected when the button 70 is pressed to trigger a dispense.

The dose selector 80 is radially constrained to the housing 10 and rotationally constrained to the button 70. When depressed, the button 70 is rotationally constrained to the housing 10 via a splined engagement.

The drive spring 90 is attached at one end to the housing 10 and at the other end to the dose setting element 60. The drive spring 90 is pre-wound upon assembly, such that it applies a torque to the dose setting element 60 when the mechanism is at zero units dialed. The action of rotating the dose selector 80, to set a dose, rotates the dose setting element 60 relative to the housing 10, and charges the drive spring 90.

The gauge element 110 is constrained to prevent rotation but allow translation relative to the housing 10 via a splined interface. The gauge element 110 has helical features on its inner surface which engage with the helical thread cut 63 in the dose setting element 60 such that rotation of the dose setting element 60 causes axial translation of the gauge element 110. These helical features on the gauge element 110 also create stop abutments against the end of the helical cut in the dose setting element 60 to limit the minimum and maximum dose that can be set.

The clutch plate 120 is splined to the dose setting element 60 when in the dialing and dispense conditions. On entry to the reset condition the dose setting element 60 moves axially in a distal direction, disconnecting this spline interface with the clutch plate 120. The clutch plate 120 is also coupled to the drive sleeve 40 via a ratchet interface 42, 121, which occurs on an axial abutment. The ratchet provides a detented position between the dose setting element 60 and drive sleeve 40 corresponding to each dose increment, and engages different ramped tooth angles during clockwise and anti-clockwise relative rotation.

The axial position of the drive sleeve 40, clutch plate 120 and button 70 is defined by the action of the trigger spring 130, which applies a biasing force on the drive sleeve 40 in the proximal direction. In the at rest position, this ensures that splines of the button 70 are engaged with splines 64 the dose setting element 60 and that the drive sleeve 40 teeth 41 are engaged with the reset plate 150.

The bearing 140 is axially constrained to the piston rod 30 and acts on the bung within the liquid medicament cartridge 100.

The reset plate 150 is rotationally splined to the housing 10 and biased in a distal direction against the cartridge holder 20 by the trigger spring 130. The reset plate 150 contains spline teeth 151 that prevent rotation of the drive sleeve 40 during dialing of the device, and clips to prevent axial motion of the dose setting element 60 in the dialing and dispense conditions. The reset plate 150 clips into the outer housing 10 to limit its range of motion in the proximal direction.

The cartridge holder spring 160 acts between the outer housing 10 and the cartridge 100 to bias the cartridge 100 in the distal direction.

The main functions of the device are now described in more detail: With the device in the at rest condition as shown in FIG. 3, the dose setting element 60 is positioned against its zero dose abutment with the gauge element 110, and the button 70 is not depressed. Dose marking '0' on the dose setting element 60 is visible through the window 11$b$ of the housing 10 and gauge element 110. The drive spring 90, which has a number of pre-wound turns applied to it during assembly of the device, applies a torque to the dose setting element 60 and is prevented from rotating by the zero dose abutment. It is also possible to "back-wind" the mechanism slightly due to an offset between the zero dose stop and the angular offset of the drive sleeve spline teeth 41. This has the effect of preventing possible webpage when a dose is dialed and the zero dose abutment is disengaged.

The user selects a variable dose of liquid medicament by rotating the dose selector 80 clockwise, which generates an identical rotation in the dose setting element 60. Rotation of the dose setting element 60 causes charging of the drive spring 90, increasing the energy stored within it. As the dose setting element 60 rotates, the gauge element 110 translates axially due to its threaded engagement thereby showing the value of the dialed dose. The gauge element 110 has flanges either side of the window area 111 which cover the numbers printed on the dose setting element 60 adjacent to the dialed dose to ensure only the set dose number is made visible to the user.

One specific element of this type of mechanism is inclusion of a visual feedback feature in addition to the discrete dose number display typical on devices of this type. The distal end of the gauge element 110 creates a sliding scale (although this could be formed using a separate component engaged with the dose setting element 60 on a different helical track if desired) through the small window 11$a$ in the housing 10. As a dose is set by the user the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge element 110 feature provides feedback to the user during dispense regarding dispense progress without the need to read the dose number itself.

The gauge element 110 display may be formed by an opaque sliding element revealing a contrasting colored component underneath. Alternatively, the concealed component may be printed with coarse dose numbers or other indices to provide more precise resolution. In addition, the gauge element 110 display simulates a syringe action during dose set and dispense.

The drive sleeve 40 is prevented from rotating as the dose is set due to the engagement of its splined teeth 41 with the reset plate 150, and the clutch plate 120 rotated due to the engagement of its splined teeth with teeth of the dose setting element 60. Relative rotation must therefore occur between the clutch plate 120 and drive sleeve 40 via the ratchet interface 121, 42.

The user torque required to rotate the dose selector 80 is a sum of the torque required to wind up the drive spring 90, and the torque required to overhaul the ratchet feature. The trigger spring 130 is designed to provide an axial force to the ratchet feature and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the trigger spring 130, the clockwise ramp angle of the ratchet, the friction coefficient between the mating surfaces and the mean radius of the ratchet features.

As the user rotates the dose selector 80 sufficiently to increment the mechanism by 1 increment, the clutch plate 120 rotates relative to the drive sleeve 40 by 1 ratchet tooth 121, 42. At this point the ratchet teeth re-engage into the next detented position. An audible click is generated by the ratchet re-engagement, and tactile feedback is given by the change in torque input required.

Relative rotation of the dose setting element 60 and the drive sleeve 40 causes the last dose nut 50 to travel along its threaded path, towards its last dose abutment on the drive sleeve 40.

With no user torque applied to the dose selector 80, the dose setting element 60 is now prevented from rotating back due to the torque applied by the drive spring 90, solely by the ratchet engagement 121, 42 between the clutch plate 120 and the drive sleeve 40. The torque necessary to overhaul the ratchet in the anti-clockwise direction is a function of the axial load applied by the trigger spring 130, the anti-clockwise ramp angle of the ratchet, the friction coefficient between the mating surfaces and the mean radius of the ratchet features. The torque necessary to overhaul the ratchet must be greater than the torque applied to the dose setting element 60 (and hence clutch plate 120) by the drive spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interfaces 121, 42 between the dose setting element 60 and drive sleeve 40 is repeated for each dose increment. Additional energy is stored within the drive spring 90 for each dose increment and audible and tactile feedback is provided for each increment dialed by the re-engagement of the ratchet teeth. The torque required to rotate the dose selector 80 increases as the torque required to wind up the drive spring 90 increases. The torque required to overhaul the ratchet in the anti-clockwise direction must therefore be greater than the torque applied to the dose setting element 60 by the drive spring 90 when the maximum dose has been reached.

If the user continues to increase the selected dose until the maximum dose limit is reached, the dose setting element 60 engages with its maximum dose abutment on the gauge element 110. This prevents further rotation of the dose setting element 60, clutch plate 120 and dose selector 80.

Depending on how many increments have already been delivered by the mechanism, during selection of a dose, the last dose nut 50 may contact its last dose abutment with the drive sleeve 40. The abutment prevents further relative rotation between the dose setting element 60 and the drive sleeve 40, and therefore limits the dose that can be selected. The position of the last dose nut 50 is determined by the total number of relative rotations between the dose setting element 60 and drive sleeve 40, which have occurred each time the user sets a dose.

With the mechanism in a state in which a dose has been selected, the user is able to deselect any number of increments from this dose (dose correction). Deselecting or decreasing a dose is achieved by the user rotating the dose selector 80 anti-clockwise. The torque applied to the dose selector 80 by the user is sufficient, when combined with the torque applied by the drive spring 90, to overhaul the ratchet 121, 42 between the clutch plate 120 and drive sleeve 40 in the anti-clockwise direction. When the ratchet is overhauled, anti-clockwise rotation occurs in the dose setting element 60 (via the clutch plate 120), which returns the dose setting element 60 towards the zero dose position, and unwinds the drive spring 90. The relative rotation between the dose setting element 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially.

When the button 70 is depressed, splines between the button 70 and dose setting element 60 are disengaged, rotationally disconnecting the button 70 and dose selector 80 from the delivery mechanism. Splines on the button 70 also engage with splines on the housing 10 (so that the dose selector 80 and button 70 do not rotate during dispense). The button 70 force acts on the drive sleeve 40, via the clutch plate 120, which travels axially and disconnects the splined engagement with the reset plate 150, allowing rotation of the drive sleeve 40. The force on the clutch plate 120 to drive sleeve 40 ratchet is increased by compression of the trigger spring 130, causing these components to spin together rather than overhaul the ratchet 121, 42, driven by the drive spring 90 via the dose setting element 60. Rotation of the drive sleeve 40 causes the piston rod 30 to rotate due to their splined engagement, and the piston rod 30 then advances due to its threaded engagement to the outer housing 10. The dose setting element 60 rotation also causes the gauge element 110 to traverse axially back to its zero position whereby the zero dose abutment stops the mechanism. During dispense an additional splined interface 43, 61 between the drive sleeve 40 and dose setting element 60 is engaged to prevent free rotation of the dose setting element 60 if the button 70 force is removed part way through a dispense, where the clutch plate 120 to drive sleeve 40 ratchet may be momentarily unloaded while the drive sleeve 40 relocates rotational engagement with the reset plate 150 splines.

Tactile feedback during dose dispense is provided via a compliant cantilever clicker arm integrated into the button 70. This interfaces radially with ratchet features on the dose setting element 60. During dispense, as the dose setting element 60 rotates and the button 70 is rotationally coupled to the outer housing 10, the ratchet features engage with the clicker arm to produce an audible click with each dose increment delivered.

Delivery of a dose continues via the mechanical interactions described above while the user continues to depress the button 70. If the user releases the button 70, the trigger spring 130 returns the button 70 to its at rest position via the drive sleeve 40 and clutch plate 120, the drive sleeve 40 becomes rotationally constrained and delivery of a dose is halted. Once the delivery of a dose is stopped by the dose setting element 60 returning to the zero dose abutment, the user may release the button 70, which will re-engage the drive sleeve 40 spline teeth 41, 151 with the reset plate 150. The mechanism is now returned to the at rest condition.

During delivery of a dose, the drive sleeve 40 and dose setting element 60 rotate together, so that no relative motion in the last dose nut 50 occurs. The last dose nut 50 therefore travels axially on the drive sleeve 40 during dialing (and reset) only.

The mechanism also contains a cartridge holder spring 160 which acts on the rear face of the cartridge 100 to bias it in a distal direction. This aids dose accuracy as it ensures the cartridge 100 is always biased distally, removing the effect of the tolerance on the cartridge 100 length and the possibility of the cartridge 100 moving proximally when a needle is fitted to the device. In the embodiment shown, the cartridge holder spring 160 consists of a wave spring component, but it may equally be any spring means.

It is possible to angle the spline teeth 41, 151 on either the drive sleeve 40 or reset plate 150 so that when the button 70 is released the re-engagement of the spline teeth fractionally backwinds the drive sleeve 40 thereby removing the engagement of the dose setting element 60 to the gauge element 110 zero dose stop abutment. This compensates for the effect of clearances in the mechanism (for example due to tolerances) which could otherwise lead to slight advancement of the piston rod 30 and medicament dispense when the device is dialed for the subsequent dose (due to the dose setting element 60 zero dose stop no longer restraining the mechanism and instead the restraint returning to the splines between the drive sleeve 40 and housing 10).

To reset the mechanism, the user first unscrews the cartridge holder 20, which allows the trigger spring 130 to move the reset plate 150 (and consequently the dose setting element 60) axially in a distal direction. This axial travel is sufficient to disconnect the splines 41, 151 between the reset plate 150 and the drive sleeve 40 and the splines between the clutch plate 120 and the dose setting element 60. It also removes some compression from the trigger spring 130. Simultaneously, an engagement is made between spline teeth 14, 62 on the dose setting element 60 and housing 10 to lock the dose setting element 60 rotationally. This ensures that if a dose has been dialed, the drive spring 90 cannot return the dose setting element 60 to its zero position during the reset operation. The spline interface between the dose setting element 60 and button 70 remains engaged, preventing rotation of the button 70 while in the reset condition.

The user can then fit a new cartridge 100 into the cartridge holder 20, and the bearing 140 and piston rod 30 be pushed back into the mechanism. As the piston rod 30 is returned into the mechanism, a rotation in the piston rod 30 is generated due to the housing 10 thread interface. This piston rod 30 rotation causes the drive sleeve 40 to rotate due to their spline interface, which acts to backwind the last dose nut 50 towards its start position.

Towards the end of reset, the cartridge holder 20 contacts the housing 10 and at this point the bearing 140, piston rod 30 and last dose nut 50 have reached a fully reset position. Pure rotation of the cartridge holder 20 to a locked position then acts to move the reset plate 150 (and consequently dose setting element 60) in a proximal direction, reengaging splines with the drive sleeve 40 and clutch plate 120.

In the current embodiment as described above, pressing of the button 70 with the device in the reset condition will cause re-engagement of splines 41, 151 between the drive sleeve 40 and reset plate 150, preventing any further actions to reset the device until the button 70 is released. This may be prevented by controlling the relative rotational position of spline interfaces such that in the reset condition, when the dose setting element 60 is rotationally locked to the housing 10, the button 70 is prevented by the dose setting element 60 from rotating into alignment with the housing to button splines and hence cannot move axially.

The attachment of cartridge holder 20 to outer housing 10 is now described in more detail with reference to the embodiment of FIGS. 4 to 6. This embodiment is illustrated with a simplified representation of the full device. The button 70, dose selector 80, clutch plate 120, last dose nut 50, gauge 110, number sleeve 60, drive spring 90, piston rod 30, bearing 140, cartridge 100, trigger spring 130 and bias spring 160 are not shown. A simplified representation of the drive sleeve 40, outer housing 10, reset plate 150 and cartridge holder 20 are shown. Although the embodiments differ regarding the features depicted in the Figures, the interfaces of the outer housing 10, the cartridge holder 20 and the reset plate 150 (housing insert) shown in FIGS. 4 to 6 in more detail could be implemented in the device of FIGS. 1 to 3. On the other hand, the component parts and features shown in FIGS. 1 to 3 could be implemented into the device of FIGS. 4 to 6.

The embodiment shows the design of a bayonet fitment and locking mechanism for use in a medical device which is re-usable and can be reset by the user when a new cartridge is added. This mechanism is designed to lock the cartridge holder 20 to the outer housing 10 of the device, while simultaneously re-setting the positions of the piston rod 30 and reset plate 150 and consequently the drive sleeve 40, last dose nut 50, and number sleeve 60. The device is reset by pushing axially on the cartridge holder 20 in the proximal direction, which causes (due to abutment of the bung in the cartridge 100 received in the cartridge holder 20 with the bearing 140 at the distal end of the piston rod 30) the piston rod 30 to rotate helically through the outer housing 10 towards its reset position, thereby also rotating the drive sleeve 40. Towards the end of this travel, the cartridge holder 20 bayonet engages with the outer housing 10. As the drive sleeve 40 reaches its final rotational position, the reset plate 150 is moved axially by the cartridge holder 20. This causes the teeth 151 of reset plate 150 to engage with the corresponding teeth 41 of the drive sleeve 40 and prevent any further rotation of the drive sleeve 40 or piston rod 30.

Figure 4:
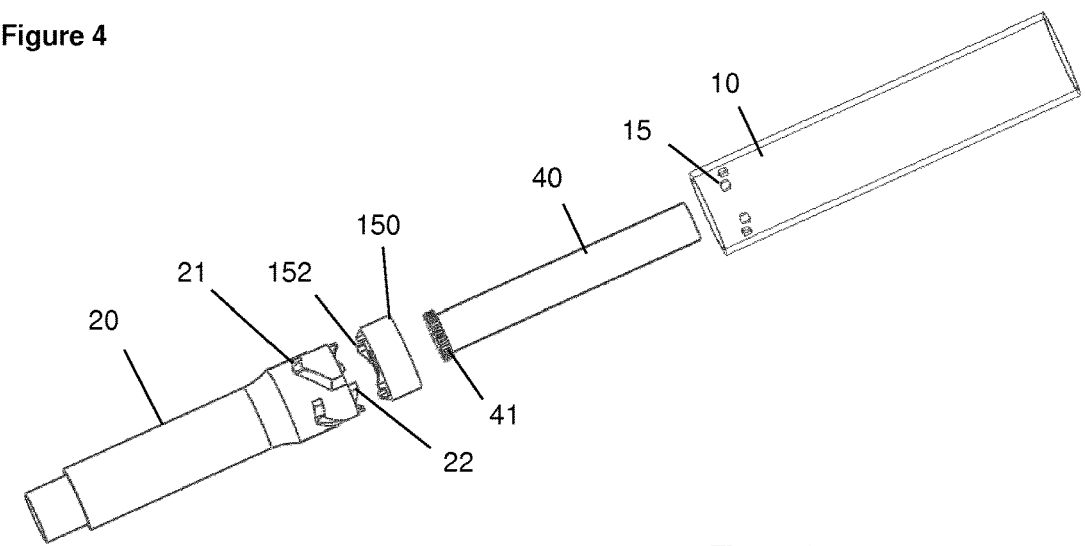
FIG. 4 shows an exploded view of the components of a drug delivery device according to a second embodiment.
Figure 5A:
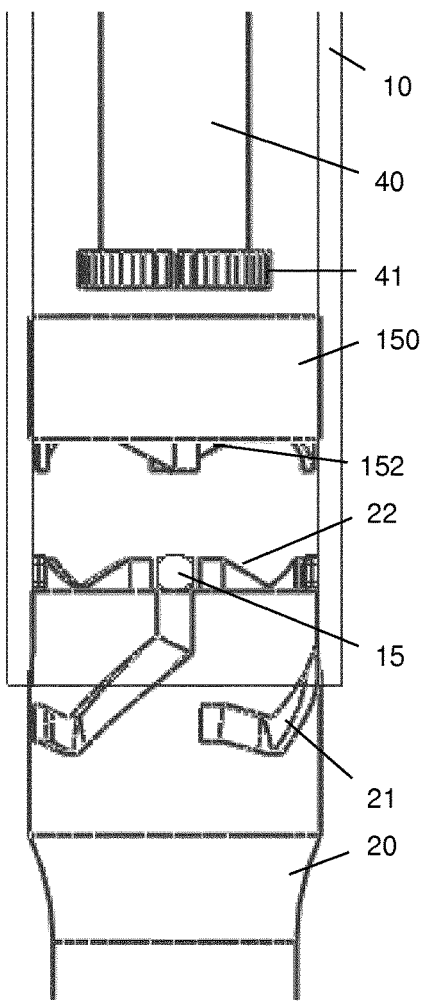
FIGS. 5*a-g* show the sequence of attaching the cartridge holder to the outer housing of the device of FIG. 3.
Figure 6:
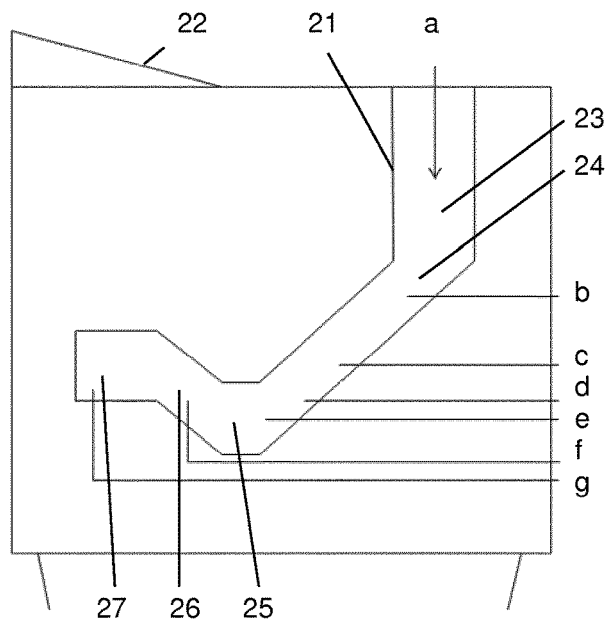
FIG. 6 shows a detail of the cartridge holder of FIG. 4.

As shown in FIGS. 4 to 6 in more detail, outer housing 10 comprises bayonet lugs 15 protruding inwardly from the inner surface of the outer housing 10 near its distal end. The cartridge holder 20 has bayonet grooves 21 on its outer proximal surface. In the embodiment shown in the Figures, the outer housing 10 comprises 4 lugs 15 and the cartridge holder 20 comprises 4 grooves 21 which are distributed around the circumference such that the lugs 15 may be introduced into the grooves 21. Each groove 21 has different portions. Starting at the proximal face of cartridge holder 20, there is a vertical portion 23 which extends parallel to the longitudinal axis I of the device. Vertical portion 23 leads at its distal end into a first sloped portion 24 which is inclined with respect to the longitudinal axis I of the device. This first sloped portion 24 is followed by first flat portion 25 extending perpendicular to the longitudinal axis I of the device. The first flat portion 25 is leads into a second sloped portion 26 which is again inclined with respect to the longitudinal axis I of the device, however, extending perpendicular to the first sloped portion 24. The second sloped portion 26 ends in a second flat portion 27 which is again perpendicular to the longitudinal axis I of the device but off-set with respect to the first flat portion 25. Further, cartridge holder 20 has at its proximal face ramps 22 forming cams and the reset plate 150, which is a housing insert, has at its distal face corresponding ramps 152. In the embodiment shown in the Figures, the cartridge holder 20 comprises 4 ramps 22 and the reset plate 150 comprises 4 ramps 152. The ramps are distributed along the circumference in a spaced manner, i.e. with a distance between each other. In FIG. 6 characters a to g indicate the position of lug 15 within groove 21 corresponding to FIGS. 5*a* to 5*g*.

As mentioned above, the reset plate 150 and number sleeve 60 (dose setting element) move axially in the distal direction upon entry to the reset condition, disengaging the reset plate 150 from the drive sleeve 40. One of the important features is that the cartridge holder 20 moves axially and rotationally on the bayonet path defined by the portion 24 of groove 21, in the proximal direction, causing compression of the cartridge bung against the piston rod 30 bearing 140, before the cartridge holder 20 returns on a different portion 26 of bayonet path 21 in the distal direction to relieve this bung compression. Simultaneously, cam features 22 on the cartridge holder 20 cause the reset plate 150 to advance axially in a proximal direction at a faster rate than the cartridge holder 20, until the reset plate 150 is in its final position relative to the drive sleeve 40. The final position of the cartridge holder 20 is retained with a detent feature.

The bayonet interface 15, 21 is designed in conjunction with the cam interface 22, 152 to provide suitable relative motion of the cartridge holder 20, reset plate 150 and outer housing 10 during reset. The timing of this motion, i.e. the stages of reset, start with the device in the reset mode when the cartridge holder 20 is ready to be pushed axially in a proximal direction against the piston rod 30 and its bearing 140.

FIG. 5*a* shows the stage when the cartridge holder 20 is pushed axially in a proximal direction against the bearing 140 of piston rod 30, causing the piston rod 30 to overhaul through the outer housing 10 and rotate the drive sleeve 40. This in turn causes the last dose nut 50 to be wound helically towards its initial position.

Figure 5B:
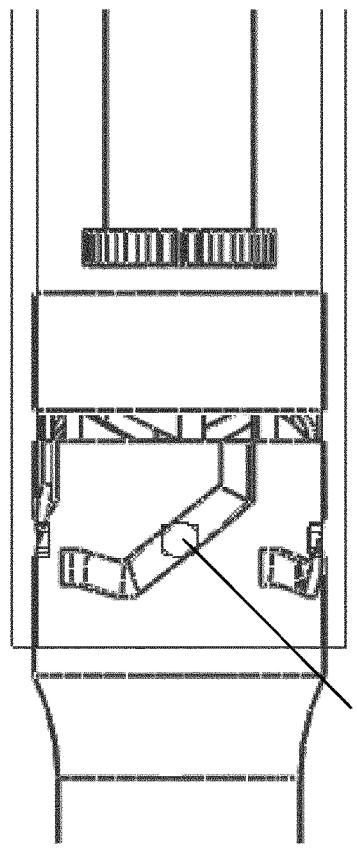

FIG. 5*b* shows the stage when the cartridge holder 20 begins to contact the reset plate 150. Therefore, as the cartridge holder 20 is rotated through the slope of groove portion 24 and advances axially in a proximal direction, the reset plate 150 is advanced axially by the same amount, against the action of the trigger spring 130 (clutch spring).

Figure 5C:
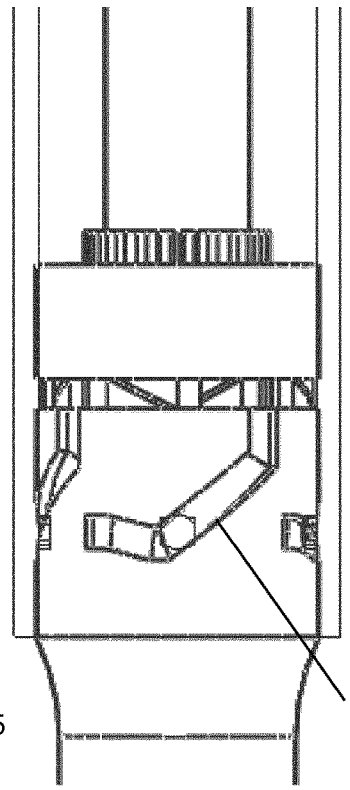

FIG. 5*c* shows the stage when the bearing 140 of piston rod 30 has been returned to its initial axial position, at which point, the drive sleeve 40 is at its initial rotational position and the last dose nut 50 is at its initial position. When the reset plate 150 has been advanced sufficiently in a proximal direction, it comes into contact with the teeth 41 on the drive sleeve 40. This must occur while lug 15 is near its distal end of groove portion 24. As the teeth 151 of reset plate 150 engage with the teeth 41 of drive sleeve 40, the drive sleeve must resolve rotationally to the nearest whole unit position. Once the rotation of the drive sleeve is locked by engagement with the reset plate 150, no further travel of the bearing 140 of piston rod 30 is achievable. Any further axial movement of the cartridge holder 20 will cause compression in the bung of the cartridge 100 (assuming a full cartridge).

Figure 5D:
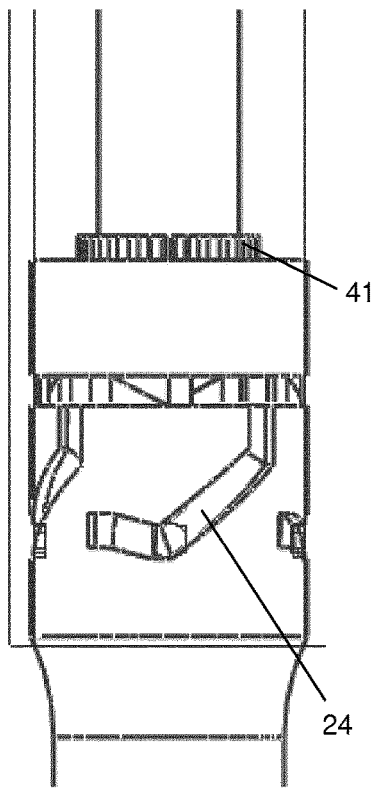

At the stage shown in FIG. 5*d*, the cam features (ramps 22) on the top of the cartridge holder 20 will begin to engage with the corresponding features 152 on the reset plate 150. This is chosen to be before the flat section (groove portion 25) of the bayonet.

Figure 5E:
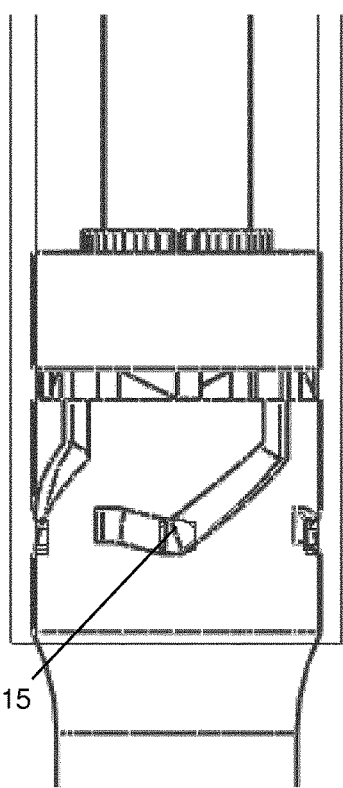

FIG. 5*e* shows the stage when the cartridge holder 20 moves in pure rotation along the flat portion 25 of the bayonet groove 21, which causes the reset plate 150 to advance axially in a proximal direction as its ramps 152 interface with the ramps 22.

Figure 5F:
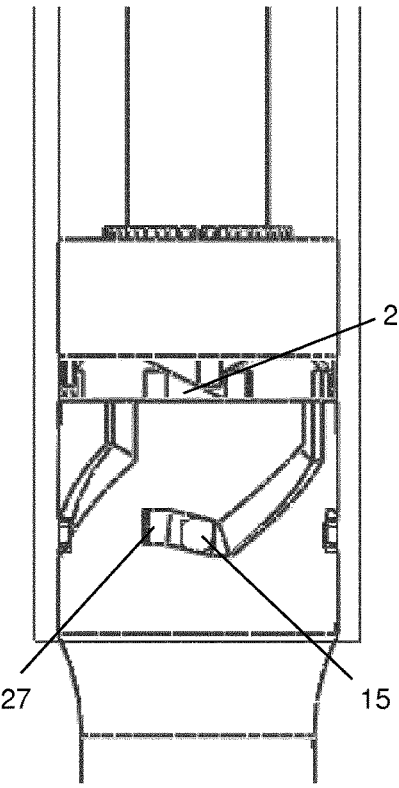

As shown in FIG. 5*f* the preferred helical path of the bayonet in groove portion 26 is opposite from preferred helical path of the first groove portion 24, such that the cartridge holder 20 begins to move axially in a distal direction, thereby reducing the compression of the cartridge bung against the bearing 140 of piston rod 30. The cam interface of ramps 22, 152 ensures that the reset plate 150 continues to move axially in a proximal direction during this phase.

Figure 5G:
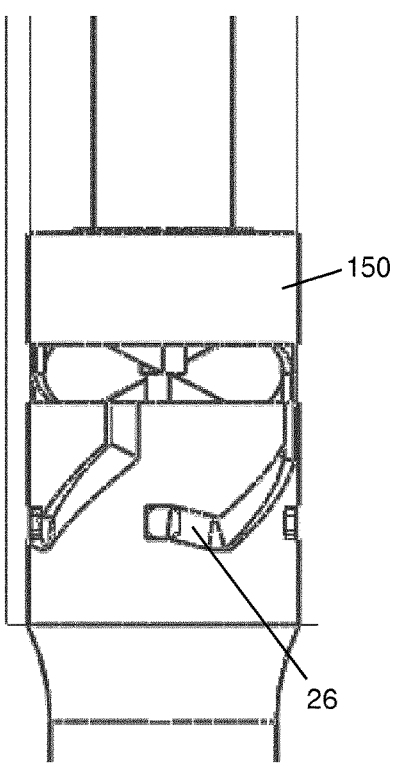

FIG. 5*g* shows the stage when the cartridge holder 20 moves onto the second flat section 27 and a detent is used to lock the cartridge holder 20 in this position. Therefore, the position of the reset plate 150 is also locked and the device is prepared for use.

The pitches of the sloped portions 24, 26 of bayonet groove 21 and the cam slopes of ramps 22, 152 are selected such that the combination of force and torque applied by the user to lock the cartridge holder 20 is not excessive, but also that the cartridge holder 20 (under the action of the clutch spring 130 and the bias spring 160) will overhaul the cam and bayonet interfaces and return to position shown in FIG. 5*a*, i.e. with lug 15 in the vertical groove portion 23, if it is released by the user before reaching the locking detent. The position of FIG. 5*c*, where the reset plate 150 first engages the drive sleeve 40, is set such that in worst case tolerance conditions, the cartridge holder 20 will always interface with the first helical sloped portion 24 of the bayonet groove 21. Therefore, the clutch spring 130 will be able to disassemble the cartridge holder 20, in all tolerance conditions, at any point before the drive sleeve position is not locked.

The mechanism provides a robust method of re-setting and locking a reusable injection device, which could be implemented across a range of devices. The combination of bayonet and cam features means that the device will not be operable unless the cartridge 100 is correctly fitted, while providing a simple user interface for re-setting the device that does not require significantly high levels of user torque or force.

| Reference Numerals: | |
| --- | --- |
| 10 | outer housing |
| 11a | opening |
| 11b | opening |
| 12 | inner thread |
| 13 | strip |
| 14 | spline |
| 15 | lug |
| 20 | cartridge holder |
| 21 | groove |
| 22 | ramp |
| 23 | vertical portion |
| 24 | first sloped portion |
| 25 | first flat portion |
| 26 | second sloped portion |
| 27 | second flat portion |
| 30 | piston rod (lead screw) |
| 31 | outer thread |
| 40 | drive sleeve |
| 41 | teeth |
| 42 | ratchet teeth |
| 43 | spline |
| 44 | thread |
| 50 | nut |
| 60 | dose setting element |
| 61 | spline |
| 62 | spline |

-continued

| Reference Numerals: | |
| --- | --- |
| 63 | thread |
| 64 | spline |
| 70 | button |
| 80 | dose selector |
| 90 | torsion spring |
| 100 | cartridge |
| 110 | gauge element |
| 111 | opening |
| 120 | clutch plate |
| 121 | ratchet teeth |
| 130 | clutch spring |
| 140 | bearing |
| 150 | reset plate |
| 151 | teeth |
| 152 | ramp |
| 160 | cartridge holder spring |
| I | longitudinal axis |

The invention claimed is:

1. A housing for a drug delivery device comprising an outer housing with a distal end and a proximal end, a housing insert, which is rotationally constrained to the outer housing and guided axially movable relative to the outer housing, and a cartridge holder, which is attachable to the distal end of the outer housing, wherein the cartridge holder comprises proximally facing ramps and the housing insert comprises corresponding distally facing ramps, wherein one of the cartridge holder and the outer housing defines at least one groove and the other of the cartridge holder and the outer housing comprises at least one lug to couple the outer housing and the cartridge holder to one another, and the at least one groove comprises a first sloped portion inclined such that the cartridge holder is moved proximally relative to the outer housing upon a rotational attaching movement of the cartridge holder relative to the housing insert and a second sloped portion inclined such that the cartridge holder is moved distally relative to the outer housing upon the rotational attaching movement of the cartridge holder relative to the housing insert.

2. The housing according to claim 1, wherein the proximally facing ramps and the distally facing ramps engage at least when the at least one lug is in the second sloped portion of the at least one groove and are inclined such that the housing insert is moved proximally relative to the outer housing and the cartridge holder upon the rotational attaching movement of the cartridge holder relative to the housing insert.

3. The housing according to claim 1, wherein the at least one groove further comprises at least one flat portion inclined such that the cartridge holder is not moved axially relative to the outer housing upon the rotational attaching movement of the cartridge holder relative to the housing insert.

4. The housing according to claim 3, wherein the at least one groove comprises a first flat portion, interposed between the first sloped portion and the second sloped portion, and a second flat portion, located after the second sloped portion, the first and second flat portions being engageable using the rotational attaching movement of the cartridge holder relative to the housing insert.

5. The housing according to claim 4, further comprising at least one detent located on the outer housing or the cartridge holder such that the cartridge holder is rotationally locked to the outer housing when the at least one lug is in the second flat portion of the at least one groove.

6. The housing according claim 1, wherein the at least one groove further comprises at least one vertical portion inclined such that the cartridge holder is not moved rotationally relative to the outer housing upon the rotational attaching movement of the cartridge holder relative to the housing insert.

7. The housing according to claim 1, wherein the proximally facing ramps and the distally facing ramps do not engage when the at least one lug is in the first sloped portion of the at least one groove.

8. The housing according to claim 1, further comprising at least one spring biasing the housing insert in a distal direction.

9. The housing according to claim 8, wherein pitches of the first and second sloped portions and cam slopes of the ramps are selected such that the cartridge holder under an action of the at least one spring overhauls a cam interface of the ramps and an interface of the groove and the lug if it is released by a user before reaching a locking detent.

10. A drug delivery device for selecting and dispensing a number of user variable doses of a medicament, the drug delivery device comprising:
a housing comprising an outer housing with a distal end and a proximal end, a housing insert, which is rotationally constrained to the outer housing and guided axially movable relative to the outer housing, and a cartridge holder, which is attachable to the distal end of the outer housing, one of the cartridge holder and the outer housing defines at least one groove and the other of the cartridge holder and the outer housing comprising at least one lug to couple the outer housing and the cartridge holder to one another, wherein the cartridge holder comprises proximally facing ramps and the housing insert comprises corresponding distally facing ramps, and the at least one groove comprises a first sloped portion inclined such that the cartridge holder is moved proximally relative to the outer housing upon a rotational attaching movement and a second sloped portion inclined such that the cartridge holder is moved distally relative to the outer housing upon the rotational attaching movement,
a dose setting element rotatable relative to the outer housing during dose setting and dose dispensing,
a drive member coupled to the dose setting element via a clutch, and
a piston rod coupled to the outer housing and to the drive member,
wherein the housing insert is axially constrained to the dose setting element.

11. The drug delivery device according to claim 10, further comprising a clutch for rotationally coupling the outer housing and the dose setting element depending on an axial position of the dose setting element relative to the outer housing.

12. The drug delivery device according to claim 10, further comprising a clutch for rotationally coupling the housing insert and the drive member depending on an axial position of the drive member relative to the housing insert.

13. The drug delivery device according to claim 12, wherein the drive member is axially movable relative to the outer housing between a dose setting position in which the drive member is rotationally constrained to the outer housing via the housing insert and a dose dispensing position in which the drive member is rotatable relative to the housing insert and the outer housing.

14. The drug delivery device according to claim 13 comprising at least one spring that biases the drive member into its dose setting position.

15. The drug delivery device according to claim 10, wherein the outer housing comprises an inner thread and wherein the piston rod is rotationally constrained to the drive member and comprises an outer thread engaging the inner thread.

16. The drug delivery device according to claim 10, further comprising a drive spring interposed between the outer housing and the dose setting element.

17. The drug delivery device according to claim 10, further comprising a gauge element radially interposed between the outer housing and the dose setting element, wherein the gauge element is axially movable relative to the outer housing and in a threaded engagement with the dose setting element.

18. The drug delivery device according to claim 10, further comprising a cartridge containing a medicament.

19. A method of resetting and locking a drug delivery device comprising
unscrewing a cartridge holder from an outer housing and removing a used cartridge from the cartridge holder,
inserting a new cartridge into the cartridge holder, wherein the new cartridge physically pushes a piston rod, a bearing, and a last dose nut further into the cartridge holder, to a starting position, and;
locking the cartridge holder to the outer housing using a combination of a bayonet and cam features by rotating the cartridge holder relative to the outer housing, wherein rotating the cartridge holder relative to the outer housing causes the cartridge holder to move proximally relative to the outer housing and then causes the cartridge holder to move distally relative to the outer housing, and locking the cartridge holder also locks a reset plate into an operable position.

20. The method of claim 19, wherein a locking feature at an end of a bayonet pathway detents a lug, wherein the drug delivery device is only operable after the lug is detented.

* * * * *

UNITED STATES PATENT AND TRADEMARK OFFICE
CERTIFICATE OF CORRECTION

PATENT NO. : 10,653,840 B2
APPLICATION NO. : 15/514997
DATED : May 19, 2020
INVENTOR(S) : Oliver Charles Gazeley and Paul Richard Draper It is certified that error appears in the above-identified patent and that said Letters Patent is hereby corrected as shown below:

In the Claims

Column 23, Line 1, Claim 6, after "according", insert -- to --

Signed and Sealed this
Seventh Day of June, 2022

Katherine Kelly Vidal
*Director of the United States Patent and Trademark Office*